US006198395B1

(12) United States Patent
Sussman

(10) Patent No.: US 6,198,395 B1
(45) Date of Patent: Mar. 6, 2001

(54) SENSOR FOR SIGHT IMPAIRED INDIVIDUALS

(76) Inventor: Gary E. Sussman, 7385 Old Mill Rd., Bloomfield, MI (US) 48301

(*) Notice: Subject to any disclaimer, the term of this patent is extended or adjusted under 35 U.S.C. 154(b) by 0 days.

(21) Appl. No.: 09/020,969

(22) Filed: Feb. 9, 1998

(51) Int. Cl.[7] .................................................. G08B 23/00
(52) U.S. Cl. ................................ 340/573.1; 340/407.1; 434/116; 342/24
(58) Field of Search .............................. 340/573.1, 407.1; 348/62; 434/116; 342/24

(56) References Cited

U.S. PATENT DOCUMENTS

| | | |
|---|---|---|
| 3,654,477 | 4/1972 | Benjamin, Jr. . |
| 3,800,082 | 3/1974 | Fish . |
| 3,907,434 * | 9/1975 | Coles ................................ 340/407.1 |
| 3,993,407 | 11/1976 | Moricca et al. . |
| 3,996,950 | 12/1976 | Mier . |
| 4,008,456 * | 2/1977 | Ewart ................................ 340/407.1 |
| 4,280,204 | 7/1981 | Elchinger . |
| 4,322,744 * | 3/1982 | Stanton ................................ 434/116 |
| 4,378,569 * | 3/1983 | Dallas, Jr. et al. .................... 358/94 |
| 4,462,046 | 7/1984 | Spight . |
| 5,047,994 | 9/1991 | Lenhardt et al. . |
| 5,097,326 | 3/1992 | Meijer . |
| 5,097,856 | 3/1992 | Chi-Sheng . |
| 5,107,467 | 4/1992 | Jorgenson et al. . |
| 5,341,346 | 8/1994 | Youlton . |
| 5,347,273 | 9/1994 | Katiraie . |
| 5,442,592 | 8/1995 | Toda et al. . |
| 5,467,634 | 11/1995 | Brady et al. . |
| 5,487,669 | 1/1996 | Kelk . |
| 5,573,001 | 11/1996 | Petrofsky et al. . |
| 5,807,111 * | 9/1998 | Schrader ................................ 434/116 |
| 5,818,381 * | 10/1998 | Williams ................................ 342/24 |

OTHER PUBLICATIONS

Visionics Corporation, *A Brighter Picture A Fuller Life*, "The Visionics Low Vision Enhancement System", 4 pages, Visionics Corp., Minneapolis, MN.

Susan Gormezano, O.D., Brochure: *Understanding the Low Vision Enhancement System*, 4 pages (plus cover), Low Vision Associates, P.C., Southfield, MI.

*WalkMate brochure*, Ultrasonic Mobility Enhancement System, 1993, 4 pages, Distributed by Maxi Aids, Farmingdale, NY.

* cited by examiner

*Primary Examiner*—Daniel J. Wu
*Assistant Examiner*—John Tweel, Jr.
(74) *Attorney, Agent, or Firm*—Brooks & Kushman P.C.

(57) ABSTRACT

A sensory system and method for a visually impaired user includes an array of laser transmitters for transmitting laser signals in given areas corresponding to each of the laser transmitters. An array of laser sensors are provided for receiving laser signals reflected from objects in the corresponding given areas with each laser sensor corresponding to a respective one of the array of laser transmitters. The time between transmitted and received laser signals of a laser transmitter and the respective laser sensor is indicative of the distance between the user and an object in the corresponding given area. A processor is operable with the laser transmitters and laser sensors to effect scanning of the given areas by the array and to process the transmitted and received signals to determine the distance between the user and an object in the given areas. A feedback system is operable with the processor for generating a feedback signal for each of the laser sensors as a function of the received laser signals. The sensing system and method may also include an array of ultrasonic transducers.

20 Claims, 2 Drawing Sheets

SENSOR FOR SIGHT IMPAIRED INDIVIDUALS

TECHNICAL FIELD

The present invention relates generally to obstacle detection devices for the blind and, more particularly, to a sensing array for the blind.

BACKGROUND ART

A variety of mobility aids have been developed to provide the blind with a means of traveling independently, confidently, and quickly. These aids include sensory devices for sensing potential obstacles. The sensory devices typically transmit a signal in a beam towards an area and then listen to receive a signal reflected off of an object in the area. Because the propagation velocity of the signal is known, the time between the transmit and reflected signals is indicative of the distance of the object from the sensory device.

A primary disadvantage with the prior art is in "sensing" the space between objects, as well as sensing the general outline of the objects themselves. For example, a blind person walking down the street would like to distinguish between people, mail boxes, trees, etc., and of the gaps between them. In essence, the blind person would like to be able to form a mental picture or "footprint" of the surrounding environment. The blind person would also like to be able to form the mental picture from tactile stimulation and/or auditory signals as quickly and accurately as possible. The prior art is devoid of such a sensory device.

SUMMARY OF THE INVENTION

Accordingly, it is an object of the present invention to provide a sensory system which enables a visually impaired user to obtain a mental picture of the surrounding environment.

It is another object of the present invention to provide a sensory system having an array of transmitters and sensors operable to enable the visually impaired user to obtain a mental picture of the surrounding environment.

It is a further object of the present invention to provide a sensory system having an array of ultrasonic transducers.

It is still another object of the present invention to provide a sensory system having an array of laser transmitters and laser sensors.

In carrying out the above objects and other objects, a sensory system for a visually impaired user is provided. The sensory system includes an array of laser transmitters for transmitting laser signals in given areas corresponding to each of the laser transmitters. The system further includes an array of laser sensors for receiving laser signals reflected from objects in the given areas with each laser sensor corresponding to a respective one of the laser transmitters. The time between transmitted and received laser signals is indicative of the distance between the user and an object in the corresponding given area.

A processor is operable with the laser transmitters and laser sensors to effect scanning of the given areas by the array. The processor also processes the transmitted and received signals to determine the distance between the user and objects in the given areas. A feedback system is operable with the processor for generating a feedback signal for each of the laser sensors as a function of the received laser signal.

Further, in carrying out the above objects and other objects, the present invention provides a method for a visually impaired user. The method includes transmitting laser signals in given areas corresponding to respective positions. The laser signals reflected from objects in the corresponding given areas are then received at the respective positions. The time between transmitted and received laser signals at the respective positions is indicative of the distance between the user and an object in the corresponding given area.

The transmission and reception of the laser signals at the respective positions may be enabled and disabled periodically to effect scanning of the given areas. A feedback signal is generated for each of the positions as a function of the received laser signal.

The advantages accruing to the present invention are numerous. The sensory system provides a visually impaired user with a footprint mental picture of the environment by scanning horizontally and vertically across a sensor array.

These and other features, aspects, and embodiments of the present invention will become better understood with regard to the following description, appended claims, and accompanying drawings.

BEST MODES FOR CARRYING OUT THE INVENTION

Figure 1:
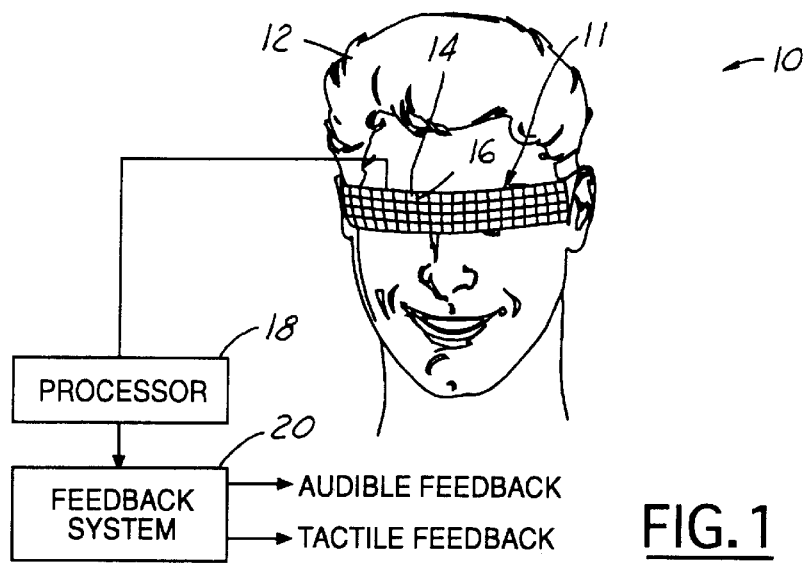
FIG. 1 is a block view of an embodiment of the sensory system of the present invention.

Referring now to FIG. 1, an embodiment of a sensory system 10 is shown. Sensory system 10 includes a visor device 11 worn by a visually impaired user 12. Visor device 11 may extend on the face of user 12 between the ears of the user to provide feedback on objects in front of the user. Visor device 11 may also be configured to be wrapped around the head and face of user 12 (not specifically shown) to provide feedback on objects around the user. In this configuration, visor device 11 enables user 12 to have 360° peripheral vision.

Visor device 11 includes an array of laser transmitters 14 and laser sensors 16. As shown in FIG. 1, visor device 11 is divided into a plurality of segments. Each segment has a transmitter 14 and a corresponding sensor 16.

Transmitters 14 transmit laser signals along a highly directional beam at a given area in front of, or around, user 12. Transmitters 14 are arranged and pointed such that each transmitter transmits toward a zone in the given area. Preferably, each transmitter 14 transmits a laser signal perpendicular to user 12. Thus, the given area is divided into a plurality of zones with each zone corresponding to one of transmitters 14.

Sensors 16 are operable to receive laser signals reflected from objects in the given area. Each sensor 16 corresponds to one of transmitters 14 and is operable to receive laser signals reflected from objects in one of the plurality zones. The time between a laser signal transmitted by one of transmitters 14 and received by a corresponding sensor 16 is indicative of the distance between user 12 and an object within the respective zone.

Sensory system 10 further includes a processor 18. Processor 18 includes a power supply for supplying power to transmitters 14 for transmitting laser signals. Processor 18 processes the laser signals received by sensors 16 to determine the time between transmitted and received signals. Processor 18 then determines the distance between user 12 and an object within a respective zone of one of transmitters 14.

Processor 18 scans the array of transmitters 14. For instance, processor 18 controls the array such that one transmitter 14 transmits a signal while the other transmitters are idle. Processor 18 is further operable to determine if sensor 16 corresponding to transmitter 14 receives a reflected signal. This process is sequentially continued with the next transmitter 14 transmitting a signal and the corresponding sensor 16 set for receiving a reflected signal.

Preferably, array of transmitters 14 are swept along a horizontal sweep and then in a vertical sweep. To effect scanning of transmitters 14, processor 18 enables and disables each of the transmitters by turning on and shutting off the supply power to the transmitters periodically.

Alternatively, processor 18 is operable to provide continuous supply power to transmitters 14 so that the transmitters are transmitting signals continuously. In this alternative embodiment, processor 18 is operable to process all of the reflected signals received by sensors 16. Processor 18 then performs multiplexing, such as time division multiplexing (TDM), with the sensors 16 such that the sensors scan the given area for reflected signals. Alternatively, processor 18 is operable such that each element of the array continuously transmits and receives signals without scanning.

A feedback system 20 is operable with processor 18 to generate audible and/or tactile feedback signals for user 12. The feedback signals are generated as a function of the received laser signal, i.e., the distance between user 12 and an object in a zone associated with a respective one of transmitters 14. From the different feedback signals generated during the scanning of the array of transmitters 14 and/or sensors 16, user 12 may form a mental picture of the objects within the surrounding environment. Because of the large numbers and highly directional capability of transmitters 14, sensory system 10 allows user 12 to distinguish objects in the given area by using the different feedback signals.

Transmitters 14 and sensors 16 of the array may be scanned by electrical or mechanical means as known to those of ordinary skill in the art. Of course, a single source transmitter/sensor pair may be used in place of the array and scanned by electrical or mechanical means.

Figure 2:
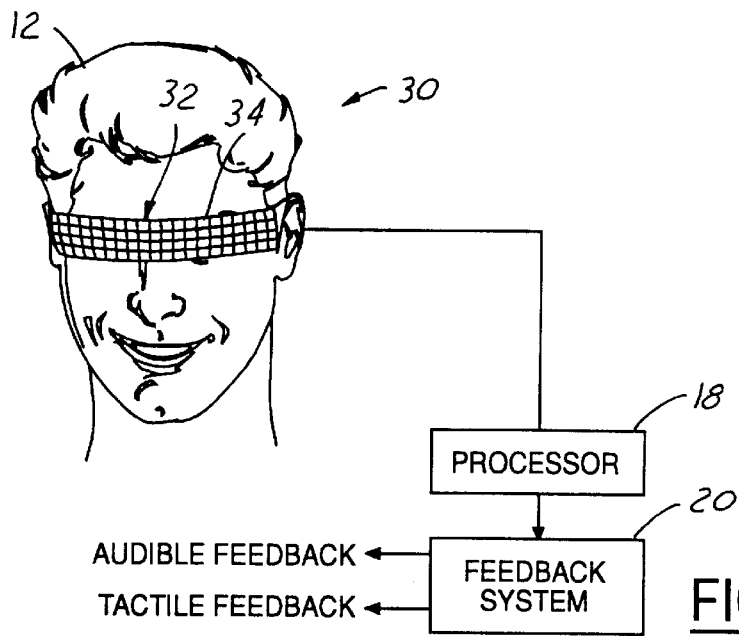
FIG. 2 is a block view of another embodiment of the sensory system of the present invention.

Referring now to FIG. 2, an alternative embodiment of a sensory system 30 is shown. Sensory system 30 differs from sensory system 10 in that visor device 32 includes an array of ultrasonic transducers 34 instead of laser transmitters 14 and laser sensors 16. Transducers 34 transmit ultrasonic signals and are arranged in an array such that each transducer transmits toward a zone in the given area. Thus, the given area in front of user 12 is divided into a plurality of zones with each zone corresponding to one of transducers 34.

Transducers 34 are also operable to receive ultrasonic signals reflected from objects in the given area. Transducers 34 have the same reception and transmission patterns so that a transducer receives ultrasonic signals reflected from an object in a respective zone in the given area. The time between an ultrasonic signal transmitted by one of transducers 34 and received by that transducer is indicative of the distance between user 12 and an object within the respective zone.

Processor 18 determines the time between transmitted and received ultrasonic signals. Processor 18 then determines the distance between user 12 and an object within a respective zone of one of transducers 34. Feedback system 20 is operable with processor 18 to generate a feedback signal for each of transducers 34 as a function of the received ultrasonic signal.

Figure 3:
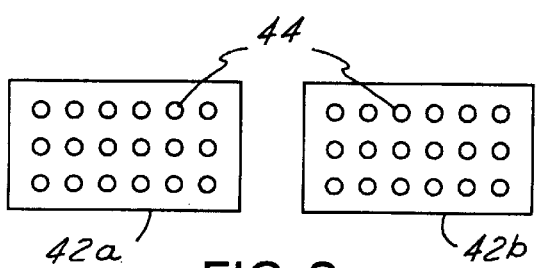
FIG. 3 illustrates two sets of vibratory feedback devices.

The feedback signals provided by feedback system 20 may take on a variety of forms. For instance, as shown in FIG. 3, feedback system 20 may be operable with two sets 42(a-b) of a plurality of vibrators 44. Vibrators 44 provide tactile stimulation to user 12. Sets 42(a–b) may be formed on an adhesive suitable for placing on the hands or sides of the face of user 16. Sets 42(a–b) may also be implanted into the body of user 12. Each vibrator 44 is associated with a respective sensor 16 (or transducer 34). Thus, each vibrator 44 corresponds to a respective zone within the given area. Other feedback forms include force-surface pressure signals.

When a sensor 16 receives a reflected signal transmitted by a corresponding transmitter 14, feedback system 20 stimulates that vibrator 44 associated with that sensor to notify user 12 of the distance between him and an object within a zone in a given area. Feedback system 20 stimulates the various vibrators 44 as the array of transmitters 14 and sensors 16 are scanned so that user 12 can form a mental picture of the surrounding environment.

Feedback system 20 varies the stimulation of a vibrator 44 as a function of the distance between user 12 and an object. For instance, the frequency or magnitude of vibration may be varied as a function of the distance between user 12 and an object. A higher frequency or magnitude may imply that the object is close to user 12. On the other hand, a lower frequency or magnitude may imply that the object is far from user 12. Vibrators 44 may also be configured to apply heat and/or force-surface pressure as a function of the distance between user 12 and an object.

Figure 4:
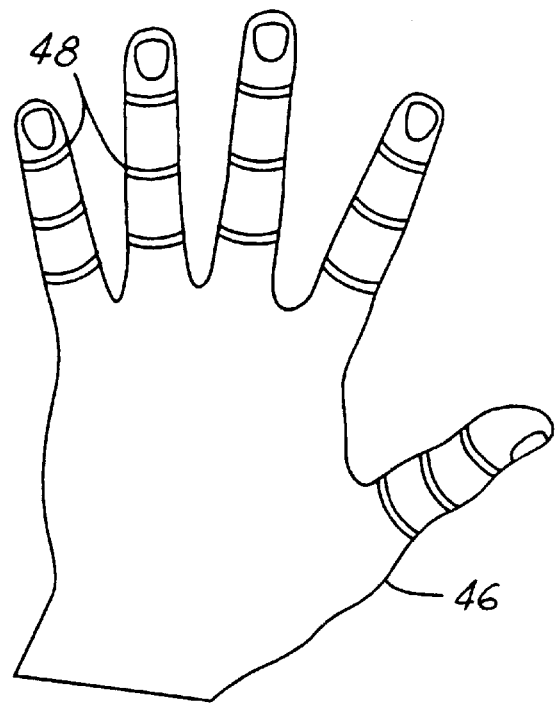
FIG. 4 illustrates a glove for providing tactile feedback.

Referring now to FIG. 4, feedback system 30 is operable with a pair of gloves 46 (only one shown) for the hands of user 12. Glove 46 is provided with muscle wires 48. Muscle wires 48 include shaped memory alloys (SMA), solenoid switches, or the like. Muscle wires 48 tighten in response to a supplied voltage. Accordingly, each muscle wire is either on or off and provides two bits of data. Glove 46 is shown in FIG. 4 as having three muscle wires 48 for each finger and thumb portion of the glove. Thus, each finger and thumb portions have eight bits of data. Each finger and thumb portion of glove 46 preferably corresponds to one of transmitters 14 and sensors 16. In this case, the array of transmitters 14 and sensors 16 consists of ten transmitter/sensor pairs with each finger and thumb portion corresponding to one of the pairs.

The eight bits of data provided by the three muscle wires 48 is indicative of detected objects in the zone covered by the corresponding pair. For example, each bit may represent three feet that an object in a zone is near user 12. Muscle wires 48 may be configured to provide different amounts of tightening. For instance, muscle wires 48 may provide strong and weak tightening in addition to no tightening. In this case, each muscle wire 48 provides three (instead of two) bits of information. As a result, twenty seven bits of data are provided by three muscle wires and each bit may represent one foot that an object in a zone is near user 12.

Figure 5:
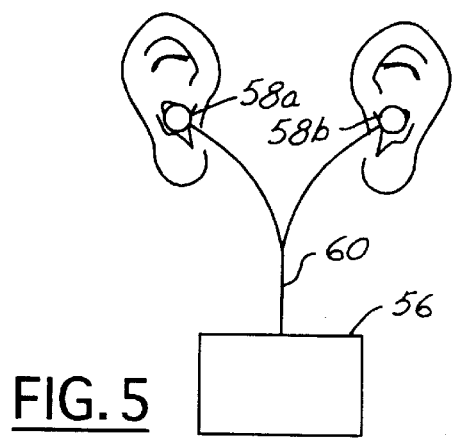
FIG. 5 illustrates an audio alarm.

Referring now to FIG. 5, feedback system 20 may also include an audio amplifier 56. Audio amplifier 56 is connected to a pair of ear speakers 58(*a–b*) by speaker cable 60. Audio amplifier 56 is associated with each of sensors 16 (or transducers 34) for providing audio feedback signals to user 12. Other devices instead of pair of ear speakers 58(*a–b*) for providing the audio feedback signals to user 12 include a single ear plug, a "bone phone", etc.

Audio amplifier 56 provides an audio feedback signal for a respective one of sensors 16. The audio feedback signals may have different tones (frequencies) for each sensor 16. For example, there may be twenty different tones for twenty sensors.

Each audio feedback signal corresponds to a respective zone within the given area. When a transmitter 14 transmits and the corresponding sensor 16 receives a laser signal, audio amplifier 56 generates a particular audio feedback signal associated with that sensor to notify user 12 of the distance between him and an object within a zone in a given area. Feedback system 20 generates the various audio feedback signals as transmitters 14 and sensors 16 are scanned so that user 12 can form a mental picture of the surrounding environment.

Audio amplifier 56 varies the volume of the audio feedback signals as a function of the distance between user 12 and an object. A higher volume may imply that the object is close to user 12. On the other hand, a lower volume may imply that the object is far from user 12.

Audio amplifier 56 may also provide audio feedback signals to user 12 as a function of the interaural volume. In this embodiment, audio amplifier 56 generates audio feedback signals having ten different tones for two sets of ten sensors. Each tone is associated with a respective sensor in the two sets. Audio amplifier 56 varies the volume of the audio feedback signal provided to each ear as a function of the distance between user 12 and objects within the two zones corresponding to the two transducers.

The feedback signals may be provided to user 12 in different patterns during scanning of the array of transmitters 14 and sensors 16. Feedback system 20 may generate the audio feedback signal for a respective sensor 16 during the time that the corresponding transmitter 14 is transmitting a laser signal. The audio feedback signal is turned off once the associated transmitter 14 and/or sensor 16 is disabled. In this embodiment, the audio feedback signals follow the scanning of the array of transmitters 14 and sensors 16. For instance, stimulation of vibrators 44 moves horizontally and vertically across the hands of user 12 during scanning. Similarly, the tones of the audio alarm signals change during scanning.

Alternatively, feedback system 20 may generate an audio feedback signal for a sensor 16 and then hold that signal for a period of time until the sensor receives a different reflected signal. Once a different reflected signal is received, feedback system 20 generates a new audio feedback signal.

In another alternative embodiment, feedback system 20 may generate an audio feedback signal for a respective sensor 16 and then hold that signal until a scanning cycle of the array of transmitters 14 and sensors 16 has been completed.

Figure 6:
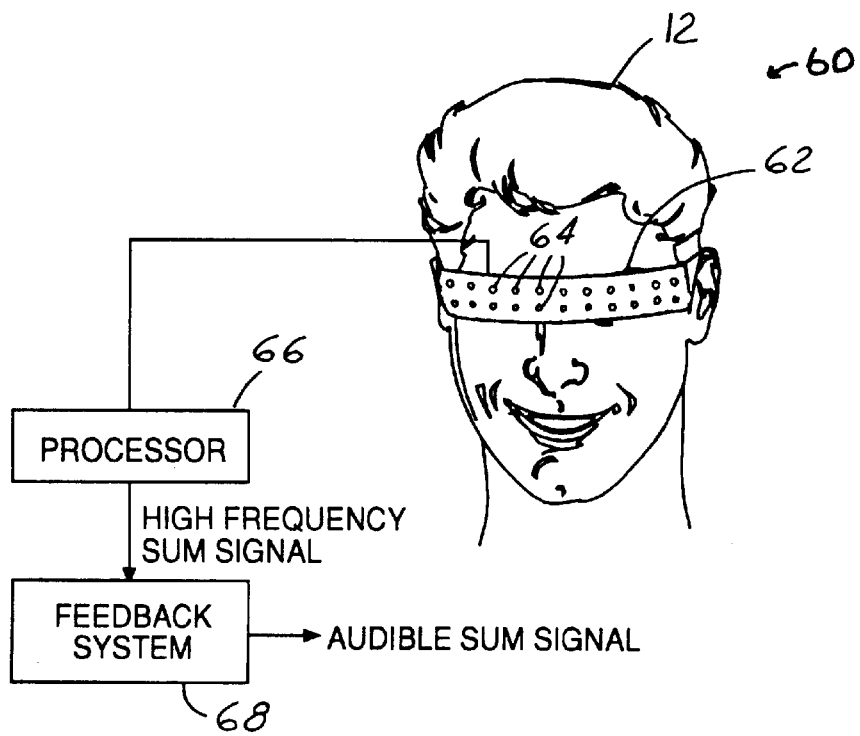
FIG. 6 is a block view of another embodiment of the present invention.

Referring now to FIG. 6, an alternative embodiment of a sensory system 60 is shown. Sensory system 60 includes a visor device 62 worn by user 12. Visor device has ultrasonic transducers 64. Sensory system 60 uses echo location similar to that used by whales, dolphins, and bats. To this end, transducers 64 transmit ultrasonic signals for a given period of time. Transducers 64 then listen to receive ultrasonic signals which are reflected from objects around user 12.

A processor 66 is operable with transducers 64 to perform signal processing. Processor 66 sums all of the received signals from transducers 64 to form a sum signal. The sum signal corresponds to the objects surrounding user 12. Thus, the sum signal changes as the objects surrounding user 12 change orientation and position.

A feedback system 68 operable with processor 66 then shifts the frequency of the sum signal down to an audible frequency for user 12. User 12 then listens to the down-shifted frequency sum signal. By being able to differentiate the sum signals through training and experience, user 12 may be able to form a mental picture of the surrounding environment.

It should be noted that the present invention may be used in a wide variety of different constructions encompassing many alternatives, modifications, and variations which are apparent to those with ordinary skill in the art. Accordingly, the present invention is intended to embrace all such alternatives, modifications, and variations as fall within the spirit and broad scope of the appended claims.

The embodiments of the sensory systems of the present invention share the feature of providing enough data to a user such that, through training and experience, the user can use the data to form a mental picture of the environment. In essence, instead of processing light for vision like sight unimpaired individuals, the sight impaired user processes the feedback data for vision.

To this end, other sensory system embodiments, such as machine vision, may be utilized. For instance, information on the surrounding environment is processed by a machine vision computer. The computer can then process the information to form a signal indicative of the surrounding environment. Through experience, a sight-impaired user can distinguish among signals to form a mental picture of the surrounding environment.

What is claimed is:

1. A sensory system for a visually impaired user comprising:
    an array of laser transmitters for transmitting laser signals in a total coverage area consisting of a plurality of given areas, each of the laser transmitters transmitting a laser signal in a corresponding given area;
    an array of laser sensors for receiving laser signals reflected from objects in the total coverage area, each of the laser sensors corresponding to a respective one of the array of laser transmitters for receiving a reflected laser signal from an object in the corresponding given area, wherein the time between transmitted and received laser signals of a laser transmitter and the respective laser sensor is indicative of the distance between the user and an object in the corresponding given area;
    a processor operable with the array of laser transmitters and laser sensors to process the transmitted and received laser signals to determine the distance between the user and objects in each of the given areas; and
    a feedback system operable with the processor for generating a feedback signal for each of the laser sensors, the feedback system generating each feedback signal as a function of the distance between an object in the corresponding given area and the user, wherein the user uses all of the feedback signals corresponding to each of the given areas to establish a mental picture of the objects in the total coverage area.

2. The system of claim 1 wherein:
    the processor is operable to periodically enable and disable the array of laser transmitters and laser sensors to effect scanning of the given areas of the total coverage area.

3. The system of claim 2 wherein:

the feedback system generates the feedback signal for each of the laser sensors during the time that the respective laser transmitter is enabled.

4. The system of claim 2 wherein:

the feedback system generates the feedback signal for each of the laser sensors until the respective laser transmitter is subsequently enabled.

5. The system of claim 2 wherein:

the feedback system generates the feedback signal for each of the laser transmitters until a scanning cycle of the array of laser transmitters has been completed.

6. The system of claim 1 wherein the alarm system comprises:

a plurality of vibrators with at least one vibrator being associated with each of the laser sensors for generating a vibratory feedback signal for the respective laser sensor.

7. The system of claim 6 wherein:

the plurality of vibrators have a given frequency of vibration, wherein the given frequency of vibration is a function of the distance between the user and the object in the corresponding given area.

8. The system of claim 1 wherein the feedback system comprises:

an audio amplifier associated with each of the laser sensors for generating an audio feedback signal for the respective laser sensor.

9. The system of claim 8 wherein:

the audio feedback signal has a given audio frequency, wherein a given audio frequency is a function of the distance between the user and the object in the corresponding given area.

10. The system of claim 8 wherein:

the audio feedback signal has a given volume, wherein a given volume is a function of the distance between the user and the object in the corresponding given area.

11. A method for a visually impaired user comprising:

transmitting a laser signal in each of a corresponding given area of a total coverage area;

receiving laser signals reflected from objects in the total coverage area, each of the reflected laser signals being reflected from an object in the corresponding given area with each received laser signal corresponding to a respective transmitted laser signal, wherein the time between transmitted and received laser signals is indicative of the distance between the user and an object in the corresponding given area;

processing the transmitted and received laser signals to determine the distance between the user and objects in each of the given areas; and generating a feedback signal for each of the received laser signals, each feedback signal generated as a function of the distance between the object in the corresponding given area and the user, wherein the user uses all of the feedback signals corresponding to each of the given areas to establish a mental picture of the objects in the total coverage area.

12. The method of claim 11 further comprising:

enabling and disabling the transmission and reception of the laser signals periodically to effect scanning of the given areas.

13. The method of claim 11 wherein:

the feedback signal is a plurality of vibrations with at least one vibrator being associated with each of the received signals for generating the feedback signal for the corresponding given areas.

14. The method of claim 13 wherein:

the plurality of vibrators have a given frequency of vibration, wherein the given frequency of vibration is a function of the distance between the user and the object in the corresponding given area.

15. The method of claim 11 wherein:

the feedback signal is an audio signal.

16. The method of claim 11 wherein:

the audio signal has given audio frequencies, wherein a given audio frequency is a function of the distance between the user and the object in the corresponding given area.

17. The method of claim 16 wherein:

the audio signal has a given volume, wherein a given volume is a function of the distance between the user and the object in the corresponding given area.

18. A sensory system for a visually impaired user comprising:

an array of ultrasonic transducers for transmitting ultrasonic signals in the environment surrounding the user, each of the ultrasonic transducers further operable to receive ultrasonic signals reflected from objects in the surrounding environment;

a processor operable with the array of ultrasonic transducers to process the reflected ultrasonic signals received by the transducers, wherein the processor processes the received signals to form a sum signal; and a feedback system operable with the processor for generating an audio feedback signal as a function of the sum signal by down shifting the frequency of the sum signal to an audible frequency, wherein the user listens to the audio feedback signal to determine objects in the surrounding environment.

19. A sensing system for a visually impaired user comprising:

an array of ultrasonic transducers for transmitting and receiving ultrasonic signals in a total coverage area consisting of a plurality of given areas corresponding to each of the ultrasonic transducers, wherein the time between transmitted and received ultrasonic signals of an ultrasonic transducer is indicative of the distance between the user and an object in the corresponding given area;

a processor operable with the array of ultrasonic transducers to process the transmitted and received ultrasonic signals to determine the distance between the user and objects in each of the given area; and a feedback system operable with the processor for generating a feedback signal for each of the ultrasonic transducers, the feedback system generating each feedback signal as a function of the distance between an object in the corresponding given area and the user, wherein the user uses all of the feedback signals corresponding to each of the given areas to establish a mental picture of the objects in the total coverage area.

20. The system of claim 19 wherein:

the processor is operable to periodically enable and disable the array of ultrasonic transducers to effect scanning of the given areas by the array.

* * * * *